US009180416B2

(12) United States Patent
Phan et al.

(10) Patent No.: US 9,180,416 B2
(45) Date of Patent: Nov. 10, 2015

(54) SYSTEM FOR USE IN BONE CEMENT PREPARATION AND DELIVERY

(75) Inventors: Christopher U. Phan, San Leandro, CA (US); Andrew Kohm, San Mateo, CA (US)

(73) Assignee: DFINE, INC., San Jose, CA (US)

( * ) Notice: Subject to any disclaimer, the term of this patent is extended or adjusted under 35 U.S.C. 154(b) by 748 days.

(21) Appl. No.: 13/474,611

(22) Filed: May 17, 2012

(65) Prior Publication Data
US 2013/0308416 A1 Nov. 21, 2013

(51) Int. Cl.
| | | |
|---|---|---|
| *B01F 5/12* | (2006.01) | |
| *B01F 13/06* | (2006.01) | |
| *B01F 11/00* | (2006.01) | |
| *B01F 13/00* | (2006.01) | |
| *B01F 15/02* | (2006.01) | |
| *A61B 17/88* | (2006.01) | |

(52) U.S. Cl.
CPC ......... *B01F 11/0071* (2013.01); *B01F 13/0023* (2013.01); *B01F 15/0258* (2013.01); *A61B 17/8805* (2013.01); *A61B 17/8822* (2013.01); *A61B 17/8827* (2013.01); *B01F 2215/0029* (2013.01)

(58) Field of Classification Search
CPC ............ B01F 11/0071; B01F 13/0023; B01F 15/0258; B01F 2215/029; A61B 17/8805; A61B 17/8822; A61B 17/8827
USPC .............................................. 366/139, 163.2
See application file for complete search history.

(56) References Cited

U.S. PATENT DOCUMENTS

| | | | |
|---|---|---|---|
| 3,349,840 A | | 10/1967 | Tope et al. |
| 3,376,999 A | | 4/1968 | De Hart et al. |
| 3,739,947 A | * | 6/1973 | Baumann et al. ............. 222/136 |
| 4,194,505 A | * | 3/1980 | Schmitz ........................ 604/138 |
| 4,377,168 A | | 3/1983 | Rzasa et al. |
| 4,492,576 A | * | 1/1985 | Dragan ........................... 433/90 |
| 4,808,184 A | * | 2/1989 | Tepic ............................ 604/518 |
| 5,051,482 A | | 9/1991 | Tepic |
| 5,130,950 A | | 7/1992 | Orban et al. |
| 5,145,250 A | | 9/1992 | Planck et al. |
| 5,190,524 A | * | 3/1993 | Wex ................................ 604/80 |
| 5,190,525 A | * | 3/1993 | Oswald et al. .................. 604/83 |
| 5,431,185 A | * | 7/1995 | Shannon et al. ........... 137/512.4 |
| 5,531,683 A | | 7/1996 | Kriesel et al. |
| 5,542,928 A | | 8/1996 | Evans et al. |
| 5,674,394 A | * | 10/1997 | Whitmore .................. 210/321.8 |
| 5,688,252 A | | 11/1997 | Matsuda et al. |
| 5,695,478 A | * | 12/1997 | Haindl .......................... 604/247 |
| 5,713,857 A | | 2/1998 | Grimard et al. |

(Continued)

FOREIGN PATENT DOCUMENTS

WO    WO 02/087416    11/2002

*Primary Examiner* — Tony G Soohoo
(74) *Attorney, Agent, or Firm* — Knobbe, Martens, Olson & Bear LLP

(57) ABSTRACT

A system for use in combining two part preparations, such as bone cement, can include a chamber for intermixing liquid and powder components, a container, a vacuum channel, and a filter. The mixing chamber can be configured to hold a non-liquid, polymer powder component of a bone cement. The container can be configured to hold a liquid component of the bone cement. The vacuum channel can direct a partial vacuum to draw the liquid component from the container into the non-liquid component in the mixing chamber to intermix the components and to thereby provide a settable bone cement.

23 Claims, 7 Drawing Sheets

(56) References Cited

U.S. PATENT DOCUMENTS

| | | |
|---|---|---|
| 5,788,711 A | 8/1998 | Lehner et al. |
| 5,810,773 A * | 9/1998 | Pesnicak .................. 604/83 |
| 5,824,084 A * | 10/1998 | Muschler .................. 128/898 |
| 5,865,798 A | 2/1999 | Grimard et al. |
| 5,899,881 A | 5/1999 | Grimard et al. |
| 6,075,067 A | 6/2000 | Lidgren |
| 6,120,174 A | 9/2000 | Hoag et al. |
| 6,122,549 A | 9/2000 | Sharkey et al. |
| 6,264,659 B1 | 7/2001 | Ross et al. |
| 6,312,149 B1 | 11/2001 | Sjovall et al. |
| 6,575,930 B1 | 6/2003 | Trombley, III et al. |
| 6,709,149 B1 * | 3/2004 | Tepic ..................... 366/139 |
| 6,736,537 B2 | 5/2004 | Coffeen et al. |
| 6,832,988 B2 | 12/2004 | Sproul |
| 6,964,667 B2 | 11/2005 | Shaolian et al. |
| 6,979,352 B2 | 12/2005 | Reynolds |
| 7,008,433 B2 | 3/2006 | Voellmicke et al. |
| 7,048,720 B1 | 5/2006 | Thorne, Jr. et al. |
| 7,048,743 B2 | 5/2006 | Miller et al. |
| 7,073,936 B1 | 7/2006 | Jonsson |
| 7,160,020 B2 | 1/2007 | Sand |
| 7,259,210 B2 | 8/2007 | Puckett et al. |
| 7,559,932 B2 | 7/2009 | Truckai et al. |
| 7,678,116 B2 | 3/2010 | Truckai et al. |
| 7,744,270 B2 * | 6/2010 | Plishka et al. ............. 366/189 |
| 8,267,571 B2 * | 9/2012 | Johansson et al. .......... 366/139 |
| 8,308,340 B2 * | 11/2012 | Ferrante et al. ........... 366/162.3 |
| 8,562,620 B2 * | 10/2013 | Truckai et al. ............. 606/94 |
| 2002/0068974 A1 | 6/2002 | Kuslich et al. |
| 2002/0191487 A1 * | 12/2002 | Sand ...................... 366/252 |
| 2004/0167617 A1 * | 8/2004 | Voellmicke et al. ........ 623/1.23 |
| 2004/0180986 A1 | 9/2004 | Bellare et al. |
| 2006/0000284 A1 | 1/2006 | Sherman et al. |
| 2006/0052794 A1 | 3/2006 | McGill et al. |
| 2006/0079834 A1 | 4/2006 | Tennican et al. |
| 2008/0188858 A1 | 8/2008 | Luzzi et al. |
| 2009/0062808 A1 | 3/2009 | Wolf, II |
| 2009/0093550 A1 | 4/2009 | Rolfes et al. |
| 2009/0171362 A1 | 7/2009 | Schaeffer |
| 2009/0281549 A1 | 11/2009 | Dixon |
| 2009/0292290 A1 * | 11/2009 | Truckai et al. ............. 606/94 |
| 2010/0091606 A1 | 4/2010 | Kwan |
| 2010/0110436 A1 | 5/2010 | Chandler et al. |
| 2010/0168271 A1 | 7/2010 | Beyar et al. |
| 2010/0262152 A1 * | 10/2010 | Shadduck et al. .......... 606/94 |
| 2013/0308416 A1 * | 11/2013 | Phan et al. ............... 366/163.2 |

\* cited by examiner

SYSTEM FOR USE IN BONE CEMENT PREPARATION AND DELIVERY

CROSS-REFERENCE TO RELATED APPLICATIONS

This application is related to the following U.S. patent and Provisional Applications: Ser. No. 12/427,531 filed Apr. 21, 2009, Ser. No. 12/578,163 filed Oct. 13, 2009, No. 61/124, 916 filed Apr. 21, 2008, and No. 61/104,979 filed Oct. 13, 2008. The entire contents of all of the above applications are hereby incorporated by reference and should be considered a part of this specification.

BACKGROUND

1. Field

Embodiments of the present disclosure relate to bone cement preparation systems.

2. Description of the Related Art

Osteoporotic fractures are prevalent in the elderly, with an annual estimate of 1.5 million fractures in the United States alone. These include 750,000 vertebral compression fractures (VCFs) and 250,000 hip fractures. The annual cost of osteoporotic fractures in the United States has been estimated at $13.8 billion. The prevalence of VCFs in women age 50 and older has been estimated at 26%. The prevalence increases with age, reaching 40% among 80-year-old women. Medical advances aimed at slowing or arresting bone loss from aging have not provided solutions to this problem. Further, the population affected will grow steadily as life expectancy increases. Osteoporosis affects the entire skeleton but most commonly causes fractures in the spine and hip. Spinal or vertebral fractures also cause other serious side effects, with patients suffering from loss of height, deformity and persistent pain which can significantly impair mobility and quality of life. Fracture pain usually lasts 4 to 6 weeks, with intense pain at the fracture site. Chronic pain often occurs when one vertebral level is greatly collapsed or multiple levels are collapsed.

Postmenopausal women are predisposed to fractures, such as in the vertebrae, due to a decrease in bone mineral density that accompanies postmenopausal osteoporosis. Osteoporosis is a pathologic state that literally means "porous bones". Skeletal bones are made up of a thick cortical shell and a strong inner meshwork, or cancellous bone, of collagen, calcium salts and other minerals. Cancellous bone is similar to a honeycomb, with blood vessels and bone marrow in the spaces. Osteoporosis describes a condition of decreased bone mass that leads to fragile bones which are at an increased risk for fractures. In an osteoporosis bone, the sponge-like cancellous bone has pores or voids that increase in dimension making the bone very fragile. In young, healthy bone tissue, bone breakdown occurs continually as the result of osteoclast activity, but the breakdown is balanced by new bone formation by osteoblasts. In an elderly patient, bone resorption can surpass bone formation thus resulting in deterioration of bone density. Osteoporosis occurs largely without symptoms until a fracture occurs.

Vertebroplasty and kyphoplasty are recently developed techniques for treating vertebral compression fractures. Percutaneous vertebroplasty was first reported by a French group in 1987 for the treatment of painful hemangiomas. In the 1990's, percutaneous vertebroplasty was extended to indications including osteoporotic vertebral compression fractures, traumatic compression fractures, and painful vertebral metastasis. Vertebroplasty is the percutaneous injection of PMMA (polymethylmethacrylate) into a fractured vertebral body via a trocar and cannula. The targeted vertebrae are identified under fluoroscopy. A needle is introduced into the vertebrae body under fluoroscopic control, to allow direct visualization. A bilateral transpedicular (through the pedicle of the vertebrae) approach is typical but the procedure can be done unilaterally. The bilateral transpedicular approach allows for more uniform PMMA infill of the vertebra.

In a bilateral approach, approximately 1 to 4 ml of PMMA is used on each side of the vertebra. Since the PMMA needs to be forced into the cancellous bone, the techniques require high pressures and fairly low viscosity cement. Since the cortical bone of the targeted vertebra may have a recent fracture, there is the potential of PMMA leakage. The PMMA cement contains radiopaque materials so that when injected under live fluoroscopy, cement localization and leakage can be observed. The visualization of PMMA injection and extravasation are critical to the technique—and the physician terminates PMMA injection when leakage is evident. The cement is injected using syringes to allow the physician manual control of injection pressure.

Kyphoplasty is a modification of percutaneous vertebroplasty. Kyphoplasty involves a preliminary step consisting of the percutaneous placement of an inflatable balloon tamp in the vertebral body. Inflation of the balloon creates a cavity in the bone prior to cement injection. The proponents of percutaneous kyphoplasty have suggested that high pressure balloon-tamp inflation can at least partially restore vertebral body height. In kyphoplasty, some physicians state that PMMA can be injected at a lower pressure into the collapsed vertebra since a cavity exists, when compared to conventional vertebroplasty.

The principal indications for any form of vertebroplasty are osteoporotic vertebral collapse with debilitating pain. Radiography and computed tomography must be performed in the days preceding treatment to determine the extent of vertebral collapse, the presence of epidural or foraminal stenosis caused by bone fragment retropulsion, the presence of cortical destruction or fracture and the visibility and degree of involvement of the pedicles.

Leakage of PMMA during vertebroplasty can result in very serious complications including compression of adjacent structures that necessitate emergency decompressive surgery. See Groen, R. et al., "Anatomical and Pathological Considerations in Percutaneous Vertebroplasty and Kyphoplasty: A Reappraisal of the Vertebral Venous System," Spine Vol. 29, No. 13, pp 1465-1471, 2004. Leakage or extravasation of PMMA is a critical issue and can be divided into paravertebral leakage, venous infiltration, epidural leakage and intradiscal leakage. The exothermic reaction of PMMA carries potential catastrophic consequences if thermal damage were to extend to the dural sac, cord, and nerve roots. Surgical evacuation of leaked cement in the spinal canal has been reported. It has been found that leakage of PMMA is related to various clinical factors such as the vertebral compression pattern, and the extent of the cortical fracture, bone mineral density, the interval from injury to operation, the amount of PMMA injected and the location of the injector tip. In one recent study, close to 50% of vertebroplasty cases resulted in leakage of PMMA from the vertebral bodies. See Hyun-Woo Do et al., "The Analysis of Polymethylmethacrylate Leakage after Vertebroplasty for Vertebral Body Compression Fractures," J. of Korean Neurosurg. Soc., Vol. 35, No. 5 (May 2004), pp 478-82, (http://www.jkns.or.kr/htm/abstract.asp?no=0042004086).

Another recent study was directed to the incidence of new VCFs adjacent to the vertebral bodies that were initially treated. Vertebroplasty patients often return with new pain caused by a new vertebral body fracture. Leakage of cement into an adjacent disc space during vertebroplasty increases the risk of a new fracture of adjacent vertebral bodies. See Am. J. Neuroradiol., 2004 February; 25(2):175-80. The study found that 58% of vertebral bodies adjacent to a disc with cement leakage fractured during the follow-up period compared with 12% of vertebral bodies adjacent to a disc without cement leakage.

Another life-threatening complication of vertebroplasty is pulmonary embolism. See Bernhard, J. et al., "Asymptomatic Diffuse Pulmonary Embolism Caused by Acrylic Cement An Unusual Complication of Percutaneous Vertebroplasty," Ann. Rheum. Dis., 62:85-86, 2003. The vapors from PMMA preparation and injection also are cause for concern. See Kirby, B. et al., "Acute Bronchospasm Due to Exposure to Polymethylmethacrylate Vapors During Percutaneous Vertebroplasty," Am. J. Roentgenol., 180:543-544, 2003.

In both higher pressure cement injection (vertebroplasty) and balloon-tamped cementing procedures (kyphoplasty), the methods do not provide for well controlled augmentation of vertebral body height. The direct injection of bone cement simply follows the path of least resistance within the fractured bone. The expansion of a balloon also applies compacting forces along lines of least resistance in the collapsed cancellous bone. Thus, the reduction of a vertebral compression fracture is not optimized or controlled in high pressure balloons as forces of balloon expansion occur in multiple directions.

In a kyphoplasty procedure, the physician often uses very high pressures (e.g., up to 200 or 300 psi) to inflate the balloon which crushes and compacts cancellous bone. Expansion of the balloon under high pressures close to cortical bone can fracture the cortical bone, typically the endplates, which can cause regional damage to the cortical bone with the risk of cortical bone necrosis. Such cortical bone damage is highly undesirable as the endplate and adjacent structures provide nutrients for the disc.

Kyphoplasty also does not provide a distraction mechanism capable of 100% vertebral height restoration. Further, the kyphoplasty balloons under very high pressure typically apply forces to vertebral endplates within a central region of the cortical bone that may be weak, rather than distributing forces over the endplate.

SUMMARY

There is a general need to provide bone cements and methods for use in treatment of vertebral compression fractures that provide a greater degree of control over introduction of cement and that provide better outcomes.

In certain embodiments, a bone cement preparation system can comprise a vacuum channel, a filter, and a saturation chamber configured to hold a non-liquid component of a bone cement. The system can further have an interface disposed between the chamber and the vacuum channel. In some embodiments, the interface can be configured to receive and position the filter between the chamber and the vacuum channel The vacuum channel can be configured to direct a partial vacuum to draw a liquid component into the non-liquid component in the chamber to mix or combine the components and to thereby provide settable bone cement.

In certain embodiments, the bone cement preparation system can further comprise a vacuum source. The vacuum source can be configured to couple to the vacuum channel and can be actuated to apply a partial vacuum through the vacuum channel to the chamber to draw the liquid into the chamber.

Some embodiments of bone cement preparation system can comprise a saturation chamber, a container, a filter, an air piston, and a base. The saturation chamber can be configured to hold a non-liquid component of a bone cement. The container can be configured to hold a liquid component of the bone cement. The container can be attached to the proximal end of the saturation chamber and the filter can be positioned at the distal end of the saturation chamber. The air piston can be connected to the base at a first connection and the filter is connected to the base at a second connection, with a flow channel between the first connection and the second connection. The base can be configured such that actuation of the air piston draws the liquid component into the non-liquid component to combine the components and to thereby provide settable bone cement.

In some embodiments the air piston can comprise a syringe having a syringe body and a plunger, and a spring to bias the plunger to an initial position. The spring may be positioned within the syringe body, such as between a distal end of the plunger and a distal wall of the syringe body. In some embodiments, the base can further include a first one way valve positioned in the flow channel between the first and second connections and optionally a second one way valve positioned in the flow channel between an outlet and at least one of the first and second connections.

A system according to some embodiments can comprise a base, a chamber, a container, a filter, and an air piston. The base can comprise first, second, and third openings, a flow channel between the first, second and third openings, and a first valve in the flow channel between the first and second openings. The chamber can hold a non-liquid component of a bone fill material and the container can hold a liquid component of the bone fill material. The filter can be positioned at a second chamber end and between the chamber and the base, the filter configured to connect to the base at the first opening. The air piston can be used to draw the liquid component into the non-liquid component to form the bone fill material, where the air piston is coupled to the base at the second opening.

In some embodiments of the system, the first valve comprises a first one-way valve. A second one-way valve may also be positioned between the third opening and at least one of the first and second openings. The air piston can take many forms such as a syringe and spring. The spring can bias a syringe plunger to an initial position.

According to some embodiments, a bone cement preparation system can comprise a saturation chamber, a funnel, a vacuum source, a base, and a flow channel. The saturation chamber can be configured to hold a non-liquid component of a two-part bone cement, the saturation chamber having distal and proximal ends. The funnel can be configured to direct a liquid component of the two-part bone cement to the saturation chamber. The funnel can be attached to or part of the proximal end of the saturation chamber. The filter can be positioned at the distal end of the saturation chamber. The vacuum source for manually creating a vacuum can comprise a housing having an internal cavity, a piston positioned within the internal cavity, and an actuation member connected to the piston and movable therewith. The piston and the internal cavity can form a vacuum chamber defining a changeable volume whose size is determined by the position of the piston within the internal cavity. The actuation member can be configured to manually increase the size of the vacuum chamber. The base can be used to position the saturation chamber in an upright position with the funnel at the top and the filter at the bottom, the vacuum source being part of or connected to the base. The flow channel can extend between the filter and the vacuum chamber, the flow channel being in fluid communication with the vacuum chamber and the saturation chamber, the system configured such that increasing the size of the vacuum chamber draws the liquid component into the non-liquid component to combine the components to thereby provide a settable bone cement. The system can be configured for manual operation to manually create a vacuum, without requiring the user to hold the vacuum source or the saturation chamber in either hand.

In some embodiments, a bone cement preparation system can comprise a base member, a saturation chamber, a funnel at the proximal end of the saturation chamber, a filter removably attached to the distal end of the saturation chamber, and a vacuum source. The filter can also be attached to the base and configured to secure the saturation chamber to the base in an upright position. The vacuum source can be part of or connected to the base. The vacuum source can comprise a housing having an internal cavity, a piston positioned within the internal cavity, and an actuation member connected to the piston for manually creating a vacuum. The system can be configured for manual operation to manually create a vacuum, without requiring the user to simultaneously hold the vacuum source and the saturation chamber.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION

Figure 1:
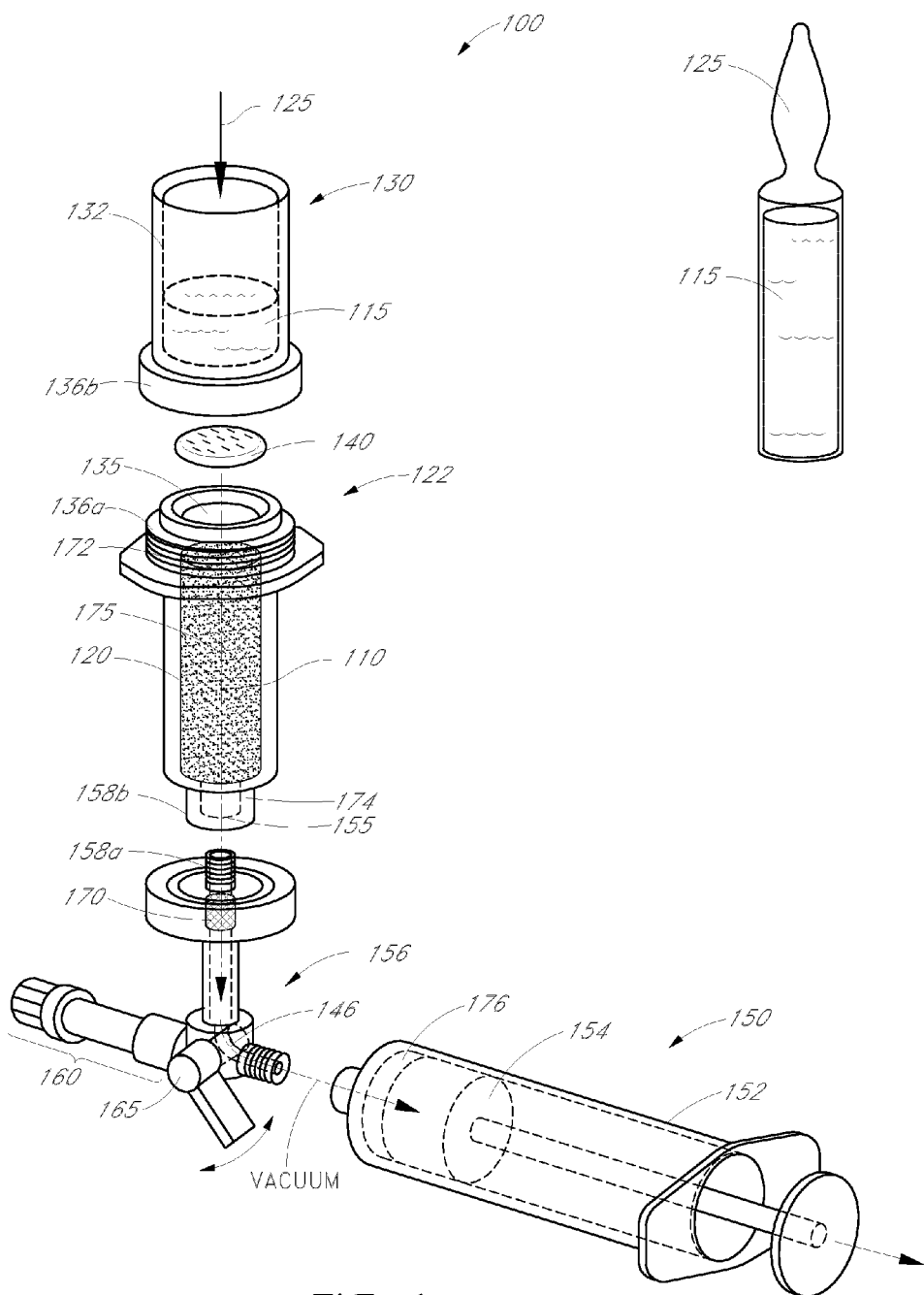
FIG. 1 is a perspective view of a system for bone cement preparation by vacuum saturation mixing of a polymer powder with a liquid monomer in accordance with some embodiments.

For purposes of understanding the principles of the invention, reference will now be made to the embodiments illustrated in the drawings and the accompanying text. As background, a vertebroplasty procedure using the system of FIG. 2 could insert parts of the system through a pedicle of a vertebra, or in a parapedicular approach, for accessing the osteoporotic cancellous bone. The initial aspects of the procedure can be similar to a conventional percutaneous vertebroplasty wherein the patient is placed in a prone position on an operating table. The patient is typically under conscious sedation, although general anesthesia is an alternative. The physician injects a local anesthetic (e.g., 1% Lidocaine) into the region overlying the targeted pedicle or pedicles as well as the periosteum of the pedicle(s). Thereafter, the physician can use a scalpel to make a 1 to 5 mm skin incision over each targeted pedicle. Thereafter, an introducer can be advanced through the pedicle into the anterior region of the vertebral body, which typically is the region of greatest compression and fracture. The physician can confirm the introducer path posterior to the pedicle, through the pedicle and within the vertebral body by anteroposterior and lateral X-Ray projection fluoroscopic views or by other methods. The introduction of infill material as described below can be imaged several times, or continuously, during the treatment depending on the imaging method. It will be understood that though a vertebroplasty procedure is described, the bone cement preparation systems and methods can be used to prepare bone cement for any desired procedure where bone cement is needed.

DEFINITIONS

"Bone cement, bone fill or fill material, infill material or composition" includes its ordinary meaning and is defined as any material for infilling a bone that includes an in-situ hardenable material or that can be infused with a hardenable material. The fill material also can include other "fillers" such as filaments, microspheres, powders, granular elements, flakes, chips, tubules and the like, autograft or allograft materials, as well as other chemicals, pharmacological agents or other bioactive agents.

"Flowable material" includes its ordinary meaning and is defined as a material continuum that is unable to withstand a static shear stress and responds with an irrecoverable flow (a fluid)—unlike an elastic material or elastomer that responds to shear stress with a recoverable deformation. Flowable material includes fill material or composites that include a fluid (first) component and an elastic or inelastic material (second) component that responds to stress with a flow, no matter the proportions of the first and second component, and wherein the above shear test does not apply to the second component alone.

"Substantially" or "substantial" mean largely but not entirely. For example, substantially may mean about 50% to about 99.999%, about 80% to about 99.999% or about 90% to about 99.999%.

"Vertebroplasty" includes its ordinary meaning and means any procedure wherein fill material is delivered into the interior of a vertebra.

"Osteoplasty" includes its ordinary meaning and means any procedure wherein fill material is delivered into the interior of a bone.

FIG. 1 is illustrative of a bone cement preparation system 100 according to certain aspects of the disclosure. In particular, FIG. 1 shows how various bone cement precursors can be connected in a bone cement preparation system 100. The bone cement precursors can include a first polymer non-liquid component 110 and a second liquid monomer component 115. Each component can be provided and maintained in separate containers prior to combination. After combination of the components, an admixture can be provided that self cures into settable bone cement, such as a PMMA cement. In other embodiments, the components can be combined to form other materials. In addition, liquid 115 and non-liquid 110 components can include respectively, one or more liquid and/or non-liquid component. For example, the non-liquid component can include two or three components as discussed in U.S. patent application Ser. No. 12/427,531, filed 21 Apr. 2009, which is incorporated by reference in its entirety and should be considered a part of this specification.

Referring to FIG. 1, the polymer non-liquid component 110 can be provided, shipped, and/or otherwise introduced prior to use, in a chamber 120 in a cement-carrying body 122. The cement-carrying body 122 can in one embodiment also be used as a delivery component for delivering bone cement into bone, as will be described in more detail below. The cement-carrying body 122 can in one embodiment be of plastic (e.g., a transparent or translucent plastic). However, the cement-carrying body 122 can be of other suitable materials. The body 122 extends along an axis 175 from a proximal end 172 to a distal end 174 with the chamber 120 or interior space in between. The proximal end 172 of the cement-carrying body 122 can have a fitting, such as, for example, a threaded fitting 136a, for connecting various other devices such as a pressurization mechanism (FIG. 2) or a receiving body 130 to the structure. The distal end 174 of the structure 122 can also have a fitting 158b (e.g., a Luer fitting) for connecting various other devices such as a delivery device, a filter, and/or a vacuum source to the structure 122 as will be described further below.

The length of the cement-carrying body 122 can in some embodiments range from about 5 cm to 20 cm, to provide an interior volume of from about 2 cc to 20 cc. In other embodiments, the cement-carrying body 122 can have other dimensions to provide other desired interior volumes. In some embodiments, the body 122 is transparent to allow viewing of monomer saturation described below. In use in a vertebroplasty procedure, one or more cement-carrying bodies 122 can be used, as a treatment of a vertebral compression fracture can use from about 2 cc to 8 cc of bone cement.

The liquid monomer component 115 can be carried in a source 125, such as an ampule. The liquid monomer component 115 can be poured or otherwise placed into an inner space 132 in receiving body 130 as indicated in FIG. 1. In some embodiments, the source 125 can include at least a part of the body 130. In some embodiments, the receiving body 130 can include a funnel.

The volume of the receiving body 130 can be sized to contain a selected volume of monomer 115 required to saturate a volume of polymer powder 110 in the cement-carrying body 122. The receiving body 130 can in one embodiment be fabricated of a clear plastic.

The receiving body 130 and the cement-carrying body 122 can couple to provide a first interface 135 wherein the liquid monomer 115 can interface with the polymer component 110. In one embodiment, the receiving body 130 is detachably coupled to body 122 by cooperating threaded fitting portions 136a and 136b. The receiving body 130 can form a fluid-tight fitting with the body 122, such as with an o-ring.

In FIG. 1, it can further be seen that a first interface surface 140 can be provided intermediate the polymer non-liquid component 110 and the liquid monomer component 115. The first interface surface 140 can control the interface 135 of the liquid 115 and polymer 110 components. The first interface surface 140 can be a seal, valve, filter etc. Where the first interface surface 140 is a seal or a valve, it can be opened in various ways including via the application of negative pressure as will be described below. The seal 140 can allow the liquid 115 to be introduced and maintained in the receiving body 130 for short or long periods of time. Thus, a practitioner may begin to prepare the bone cement independent of other activities, such as varied back table activities in the operating theatre as the physician is attending to the patient prior to the procedure.

Some embodiments do not include an interface surface 140 between the chamber 120 and the receiving body 130.

Still referring to FIG. 1, one embodiment of a vacuum source 150 is shown which can include a syringe body 152 and retractable plunger 154, or can alternatively include any other vacuum line, evacuated cartridge or the like that can produce the vacuum described below. The vacuum source 150 can be detachably coupled to the cement-carrying body 122. This can be for suctioning the liquid monomer component 115 into and through the non-liquid polymer powder component 110 disposed in chamber 120 in the body 122. The saturation of the polymer powder 110 with the monomer 115 can thus cause the biomaterial column to begin polymerization and set in post-mixing (or post-saturation) time intervals that are described further below.

The terms wetting and saturating are used interchangeably herein to describe the process of thoroughly or completely exposing the non-liquid polymer powder component to the liquid monomer component, in other words to unite the two components to thereafter cause a polymerization reaction between at least two portions of the biomaterials.

Where the vacuum source 150 connects to the cement-carrying body 122 a second interface 155 is established. This interface 155 is between the volume of polymer beads 110 and the vacuum source 150. The vacuum source 150 can be connected to body 122 either directly or by a fitting 156. The connection can be with, for example, cooperating mechanical (e.g., screw or press-fit) coupling portions indicated at 158a and 158b. The vacuum source 150 or fitting 156 can optionally include a pressure relief valve 160, and/or a valve 165 for selectively closing channel 146. In some embodiments, the pressure relief valve 160 can limit the amount of negative pressure in the syringe 152.

In some embodiments, the vacuum source 150 can include a canister pre-packaged with a suitable level of vacuum therein to provide a negative pressure source for saturating the biomaterial column with the liquid monomer. For example, the vacuum source 150 can be a vacuum/gas cartridge, similar to a $CO_2$ cartridge but with a partial vacuum inside. The vacuum canister can be coupled to cement-carrying body directly or by a fitting 156. The vacuum source 150 or the fitting 156 can have a valve 165 such as an open/close stopcock valve.

In some embodiments, the vacuum source 150 can comprise a syringe. For example, the syringe can comprise a 20 to 60 cc syringe and more particularly a 30 cc syringe. It has been found that a 30 cc syringe can provide a negative pressure of −500 mmHg or greater. The size of the syringe and the amount of desired negative pressure of certain embodiments can vary greatly and can depend on many factors. These factors can include the amount of bone cement to be prepared, the cross-section and length of the mixing chamber and the volume and dimensions of the polymer beads.

Similar to the first interface 135, the second interface 155 can have a second interface surface 170. FIG. 1 illustrates a second interface surface 170 that is a filter, but it can alternatively be a valve, seal, etc. intermediate the polymer powder or bead component 110 and the vacuum source 150. The second interface surface 170 can be configured to allow evacuated air to flow therethrough under the negative pressure but substantially prevent the flow of liquid monomer therethrough when the monomer 115 has saturated the polymer 110. Thus, in some embodiments, both the first interface 135 and the second interface 155 of the polymer component can include a valve-like mechanism to allow and/or limit fluid flows to controllably saturate the powder component with the monomer in a controlled time interval to provide a predetermined monomer/polymer ratio.

In some embodiments, where the second interface surface 170 is a filter, such as shown in FIG. 1, the filter can include a plastic (e.g., high density polyethylene) mesh filter. In some embodiments, the filter can be a metal or ceramic microporous material. The filter can in some embodiments have a mean pore dimension of about 0.05 to 10 microns. In some embodiments, the filter has a mean pore dimension of about 0.1 to 0.5 microns. In some embodiments, the filter has a mean pore dimension of about 0.2 microns. The filter pores can be configured to allow air extraction from the volume of polymer powder 110 in body 122 by initial application of a vacuum from the vacuum source 150. The liquid monomer component 115 when suctioned through the polymer powder 110 in chamber 120 can create a higher viscosity mixture akin to wet sand. The filter 170 can be configured to prevent the mixture from passing through the filter 170. The filter 170 can also function to limit liquid monomer 115 losses from the saturated mixture. This can result in a desired (e.g., an exact) volume of liquid monomer 115 being drawn by vacuum into the chamber 120 for saturating the polymer powder volume 110.

The filter 170 can advantageously facilitate the operation of the bone cement preparation system 100 according to some embodiments. This is because, the filter 170 can allow sufficient negative pressure to pass through the filter 170 to pull the liquid monomer 115 into the non-liquid 110 component, while also preventing the liquid monomer from simply passing through the chamber and into the vacuum source. For example, in some embodiments, the filter can clog to prevent flow of the liquid monomer. In some embodiments, the cement mixture can clog the filter to prevent flow of the liquid monomer. In other embodiments, the filter may swell or polymerize once contacted by the liquid monomer to prevent flow through the filter.

If an insufficient amount of liquid monomer 115 is mixed with the non-liquid 110 polymer component, the mixture will be starved, i.e. it will have insufficient liquid monomer to begin the curing process in all regions of the mixture. For example, some embodiments of the system advantageously produce a de-aerated, non-clumped and homogeneous bone cement admixture. The exact ratio for the monomer and polymer components can be provided by the packaging of these components, and the system described above can insure that substantially none of the liquid monomer escapes the system.

In some embodiments, the bone cement precursors can be combined to form a self-curing bone cement as a result of a chemical reaction when a polymer component and liquid monomer component interact, along with activators and initiators. For example, some embodiments include the mixing of a PMMA bone cement that can be provided for a treatment, such as, treating a vertebral compression fracture, setting an artificial joint, etc.

In some embodiments, the polymer component 110 is provided in a formulation of bead sizes to cooperate with the monomer volume 115 and negative pressure from the vacuum source to insure that all surfaces of the polymer beads or powder are wetted or saturated. This can be done so that the admixture does not create a polymerizing volume or other volume that clogs the intra-bead spaces to prevent monomer 115 migration from the superior region of the polymer bead volume 110 to the inferior region of the polymer beads.

It can also be important to consider the bead size of the polymer component 110 when determining the pore size of the filter 170. If the bead size is too small compared to the pore size, the initial application of negative pressure to the mixing chamber can clog the filter so that the negative pressure cannot draw the needed liquid monomer into the mixing chamber. This may occur immediately or before sufficient monomer has been drawn into the mixing chamber. If this occurs, it is unlikely that the correct monomer to polymer ratio will be obtained without some further mixing action, such as hand mixing the remaining liquid into the polymer.

The systems and methods described herein can provide many benefits such as not requiring hand mixing. The system can be faster than mixing by hand, and can minimize or eliminate clumping resulting in more uniform cement. For example, in certain embodiments the system can uniformly combine the liquid monomer and the non-liquid polymer in less than about 20 seconds, in about 10 seconds or in only a few seconds. In addition, the system can contain the fumes created by the chemical reaction when the liquid and non-liquid components are combined. For example, the fumes can be contained within the mixing chamber 120 and/or the receiving body 130. In some embodiments, at least a portion of the fumes can be drawn into the vacuum source 150.

In addition, the use of negative pressure to draw the liquid into the non-liquid can also provide certain benefits. For example, vacuum can remove the air or gas from the non-liquid. This space can be filled with the liquid to get a more even and uniform mixture. Were the liquid to be forced into the non-liquid, such as by injecting the liquid, the air is not necessarily removed. Injection can also, in some instances, result in air pockets, clumps, and other areas of non-uniformity. Hand mixing can result in similar problems. In some embodiments, the use of vacuum can substantially, if not completely, remove these problems.

Example functions of the various components are described next to illustrate how certain objectives of the disclosure are accomplished. With further reference to FIG. 1, it can be understood that the physician or nurse can first pour a predetermined volume of polymer beads 110 into chamber 120. Next, the operator can assemble and/or attach the monomer-receiving body 130 (together with optional seal 140) onto the top of cement-carrying body 122. Next, the vacuum source 150 can be coupled to the fitting 156 with a filter 170 and a stopcock valve 165. The fitting 156 with vacuum source 150 can then be attached to the cement-carrying body 122. In some embodiments, the connections between the assemblies are fluid-tight screw fittings.

Next, the operator can close the stopcock valve 165 and pull the syringe plunger 154 (or actuates another type of vacuum source) to provide a pre-determined negative pressure in bore 176 of syringe body 152. It has been found that high quality, commercially available 20 cc to 60 cc syringes can be actuated to provide about a negative pressure of −250 mmHg to −750 mmHg which can remain in the syringe for several minutes or indefinitely in some instances. Then, the operator can open a monomer source 125 (such as breaking a monomer ampule), and can pour the predetermined volume of monomer 115 into the inner space 132 of the funnel 130. The assembly 100 can be placed in a stand (not shown) to maintain the assembly in an upright position—i.e., with the axis 175 of the assembly being generally vertical so that the monomer 115 does not spill from the receiving body 130.

With the system 100 assembled including the bone cement precursors, the operator can open the stock-cock valve 155 to expose the vacuum to the inferior interface 156 of the polymer beads 110. The negative pressure can then extend through the spaces between the polymer beads 110 to thus draw the liquid monomer 115 through the volume of beads. In some embodiments, this can be done in an interval ranging between about 5 seconds and 60 seconds. It has been found that negative pressures in the range of −250 mmHg or greater, −400 mm/Hg or greater, or −500 mmHg or greater can be used to controllably saturate the volume of polymer beads 110 utilizing one embodiment of cement and monomer described in the following paragraphs.

Thus, a method of bone cement preparation can include providing a body defining a chamber for receiving bone cement precursors including a liquid monomer component 115 and at least one non-liquid polymer component 110, disposing the non-liquid component in the chamber, disposing the liquid component at a first interface with the non-liquid component, and applying a negative pressure in the range −250 mmHg or greater, −400 mm/Hg or greater, or −500 mmHg or greater to a second interface with the non-liquid component thereby causing the monomer liquid to infiltrate, saturate and wet the surfaces of the non-liquid component 110. In this method, the first interface 135 is vertically superior to the second interface 155—as the pressures can be selected to cooperate with gravity and not work against gravity.

In the embodiment described in the above method, the volume of polymer component 110 is between about 10 cc and 14 cc. The length of chamber 120 that carries the polymer component 110 is less than about 10 cm, 8 cm and 6 cm with a diameter of between 8 mm and 15 mm. In this embodiment, the volume of monomer component 115 is between about 2 cc and 4 cc. Other embodiments can have other dimensions and can use other negative pressure ranges.

In one embodiment, the polymer/monomer ratio is between 2:1 and 5:1. In some embodiments, the negative pressure can cause monomer saturation of the polymer within less that 45 seconds or less than 30 seconds.

In another aspect of the invention, the second interface surface 170 can be a polymer filter member that allows unimpeded gas or air flow at the negative pressures described above but prevents substantial flows of a liquid or monomer-polymer mixture therethrough. In one embodiment, the filter 170 can be a polymer filter with micron scale porosities ranging between 0.05 microns and 10.0 microns, and usually between 0.1 microns and 5.0 microns. In operation, the wetted filter 170 can clog and prevent liquid flows therethrough.

The filter 170 can help ensure that the polymer to monomer ratio within the chamber 120 remains in a very tight range. This is not possible with systems where the vacuum pulls too much monomer through the chamber and then out of the volume of polymer beads. As disclosed, in a preferred embodiment, the entire monomer volume remains in chamber 120 to saturate the polymer beads 110.

In another embodiment, a method for combining a liquid monomer component 115 and a non-liquid polymer component 110 of a settable bone cement includes disposing the non-liquid component 110 in a chamber 120 of a body 122 wherein the non-liquid component 110 includes a group of polymer beads without exposed or "free" benzoyl peroxide (BPO) or any other activator or initiator components. In some embodiments, all BPO (and/or other activator/initiator components) is within the polymer particles or beads, thus no BPO is free or instantly available to initiate any chemical reaction at the moment the monomer is drawn into and through the polymer bead volume. In another configuration, to eliminate free BPO a radiopacifier (such as zirconium dioxide) is milled onto the PMMA particle or bead surfaces which prevents rapid access of a monomer-polymer reaction to the BPO (and/or other activator/initiator components). These configurations of the polymer component 110 can thus allow complete monomer saturation of the polymer bead volume 110. The polymer particles are unable to react with the monomer so as to clump or clog during monomer flow therethrough within the time interval described to draw the liquid monomer into the second interface 155 with second interface surface 170.

In one embodiment, the system is configured for using a polymer powder to monomer liquid ratio of between 2:1 and 5:1 wherein the non-liquid component 110 is designed to provide no free BPO for at least 30 seconds and the vacuum saturation of the polymer component by the monomer can be accomplished with a negative pressure in the range −250 mmHg or greater, −400 mm/Hg or greater, or −500 mmHg or greater.

In another embodiment, a method for combining a liquid monomer component 115 and a non-liquid polymer component 110 of a settable bone cement can include disposing the non-liquid component 110 in a chamber 120 of a body 122 wherein the non-liquid component 110 includes a first group of beads having a first mean diameter and a second group of beads having a second mean diameter, disposing the liquid component 115 at a first interface 135 with the non-liquid component 110; and applying a negative pressure in the range −250 mmHg or greater, −400 mm/Hg or greater, or −500 mmHg or greater to a second interface 155 thereby causing wetting of the non-liquid component 110 with the liquid component 115. The first and second bead diameters can be selected to cooperate with the pressure to allow the wetting in less than about 50 seconds, 40 seconds or 30 seconds. In one embodiment, the first and second groups of beads have mean diameters, respectively of 110 microns and 35 microns. The bead diameters can be important in that the small diameter beads can be limited in volume to prevent migration and clogging of intra-bead spaces among the larger beads as the monomer is drawn rapidly through the polymer volume.

In another embodiment, the bone cement used in the system can include a monomer component and polymer component, wherein the polymer component includes a first volume of beads having a first average wt. % of benzoyl peroxide (BPO) on the basis of the total weight of the first volume and a second volume of beads having a second average wt. % of BPO on the basis of the total weight of the second volume. In this bone cement embodiment, the first group of beads can have an average cross section of less than about 100 microns, 80 microns, 60 microns or 40 microns. The second group of beads can have an average cross section of greater than about 40 microns, 60 microns, 80 microns and 100 microns. In some embodiments, the first volume has less than 0.5 wt. % of BPO and the second volume has greater than 0.5 wt. % of BPO. In some embodiments, the combined first and second volumes have less than a 5.0 wt. % of BPO or less than a 2.5 wt. % of BPO. In some embodiments, the combined first and second volumes have greater than a 0.5 wt. % of BPO or greater than a 1.0 wt. % of BPO. In other embodiments, at least a portion of the first volume is without BPO or at least a portion of the second volume is without BPO.

In another embodiment, the bone cement includes a monomer component and polymer component, wherein the polymer component includes a volume of beads carrying from 0.2% and 0.6% of BPO on the basis of the total weight of the volume, wherein at least 80% of the BPO is carried on a sub-volume of beads, the beads having a mean cross section of greater than 100 microns, and wherein less than 20% of the BPO is carried on a sub-volume of beads, the beads having a mean cross section of less than 100 microns.

In another embodiment, the bone cement includes a monomer component and polymer component, wherein the polymer component includes a volume of beads carrying from 0.2% and 0.6% of BPO on the basis of the total weight of the volume, wherein 100% of the BPO is carried on a portion of the bead volume where the beads have a mean cross section of greater than 100 microns, and wherein no BPO is carried on a portion of the bead volume where the beads have a mean cross section of less than 100 microns.

In another embodiment, the bone cement includes a monomer component and polymer component, wherein the polymer component includes a volume of beads of at least one polymeric material, wherein the polymer component carries from 0.2% and 3.0% BPO on the basis of the total weight of the volume, wherein a first portion of the bead volume carries BPO in a surface coating and wherein a second portion of the bead volume carries BPO intermixed in the at least one polymeric material.

In another embodiment, the bone cement includes a monomer component and polymer component, wherein the polymer component includes a volume of beads of at least one polymeric and from 0.2% and 3.0% BPO on the basis of the total weight of the volume, and wherein the BPO is provided in at least two of the following forms: as a surface coating on beads, as BPO particles, as BPO in microcapsules, as BPO particles within beads of a polymeric material, and as BPO in microcapsules within beads of a polymeric material.

In another method, a bone cement can be provided including a mixture of a liquid monomer component and polymer component of particles which includes distributing BPO within the mixture to provide a selected BPO availability to be wetted by the monomer component over first and second intervals, wherein the BPO availability per second over the first interval is substantially greater than the BPO availability per second over the second interval. Thereafter, the liquid monomer component and polymer component can be intermixed and then injected into bone. In this method, the selected BPO availability can be provided by at least two different particles having differing BPO configurations therein. In one embodiment, the selected BPO availability is provided by a differential BPO exposure in a surface area of the particles. In another embodiment, the selected BPO exposure is provided in part by particles having a mixed polymeric material and BPO. In yet another embodiment, the selected BPO exposure is provided in part by particles having a surface coating of BPO. In another embodiment, the selected BPO exposure is provided in part by microencapsulated BPO. In another embodiment, the selected BPO exposure is provided by particles having layers of polymeric materials and BPO.

In some embodiments of a method, the mixable bone cement can be configured to have a selected interval in which the release or exposure of BPO or other initiator is controlled. This can provide a slope of a free BPO curve over time which is positive or flat (or non-negative) for an interval post-mixing of at least 2 minutes, 4 minutes, 6 minutes, 8 minutes and 10 minutes. In another embodiment, the free BPO curve can be controlled in slope over the post-mixing period to flatten, increase in slope or decrease in slope in either direction but controlling the free BPO. By the term free BPO, it is meant the volume of BPO or other initiator that is available or exposed to the liquid monomer post-mixing.

In one specific formulation of a PMMA cement, the solid or powder component of the bone cement includes: polymethylmethacrylate polymer (PMMA) by weight of 49.6% with the nominal allowable range between 45%-55%; benzoyl peroxide (BPO) by weight is 0.40% with a nominal allowable range between 0.30-0.80%; and zirconium dioxide by weight is 50.0% with a nominal allowable range 45%-55%. In this cement formulation, the liquid component of the bone cement includes: methyl methacrylate (MMA) by weight of 99.5% with an allowable range of 98.0-99.9%; N,N-dimethyl-p-toluidine (DMPT) by weight of 0.50% with an allowable range of 0.15-0.95%; and hydroquinone (HQ) of 75 ppm with an allowable range of 30-150 ppm. In this cement formulation, the powder PMMA component as described above consists of a blend of three (3) subgroups of powders 1, 2 and 3 which are mixed in a ratio as follows: powder 1=44.28%; powder 2=36.86% and powder 3=18.86%. The nominal range of powder 1 can be from 40%-50%. The nominal range of powder 2 can be from 30%-40%. The nominal range of powder 3 can be from 40%-50%. Powder 1 consists of a target particle size of 110 microns and an allowable range between 100 and 120 microns with a molecular weight of 350,000 and an allowable range of 250,000 to 450,000; and benzoyl peroxide (BPO) at 1.0% by weight with an allowable range of 0.9% to 1.1%. Powder 2 consists of a target particle size of 80 microns and an allowable range between 70 and 90 microns with a molecular weight of 400,000 and an allowable range of 300,000 to 500,000; and benzoyl peroxide (BPO) at 1.2% by weight with an allowable range of 1.1% to 1.3%. Powder 3 consists of a target particle size of 35 microns and an allowable range between 25 and 45 microns with a molecular weight of 250,000 and an allowable range of 250,000 to 350,000; and benzoyl peroxide (BPO) at 0.0%.

Figure 2:
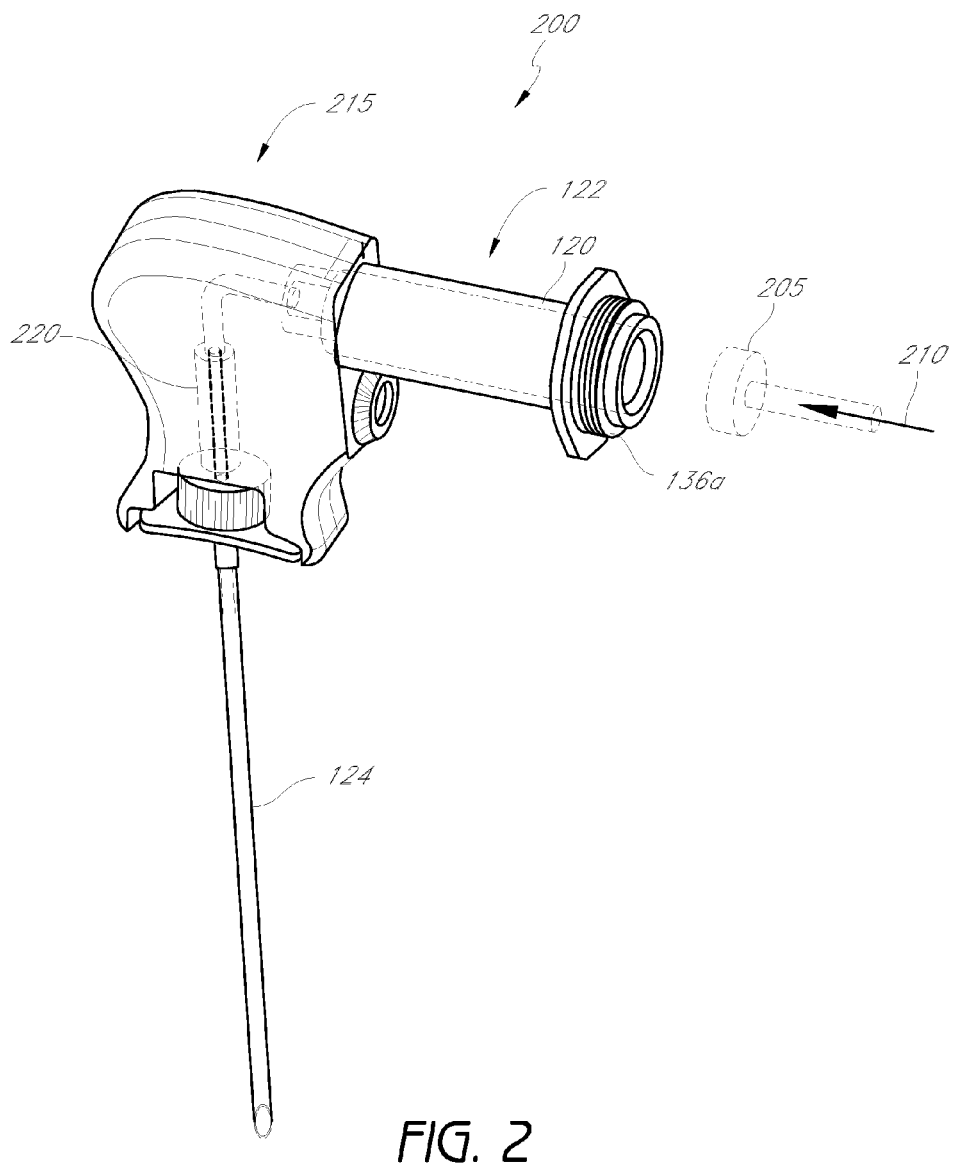
FIG. 2 is a perspective view of a component of FIG. 1 combined with additional components of a bone cement injection system.

The systems of some embodiments can further include a bone cement delivery assembly or ejection mechanism for ejecting bone cement into bone. Looking now to FIG. 2, in some embodiments, the cement-carrying body 122 can be de-coupled from the bone cement preparation system 100 and coupled to a bone cement delivery assembly 200. The bone cement delivery assembly 200 can include a bone cement injector or needle 124 that may extend into bone, such as, cancellous bone of a vertebra, and a cement activation component 215 which may include an emitter 220 for applying energy to bone cement. The bone cement delivery assembly 200 can also include a cement ejection mechanism As shown in FIG. 2, the cement ejection mechanism can include a piston or driving shaft 205 and a driving system 210. The piston 205 can be inserted into the chamber 120 to ultimately drive the bone cement through a needle 124 and into bone. The driving system 210 can actuate the piston 205. It should be appreciated that the driving system 210 can be any hand-operated syringe, hydraulic or pneumatic actuated syringe, wire-cable actuated syringe or the like. For example, the driving system 210 can include a manually advanced plunger assembly, any type of hydraulic system, $CO_2$ gas cartridge system, pneumatic system, cable drive system, screw drive system, a spring system, a motor driven system or other pump system; any of which can be computer controlled with a microprocessor that executes one or more control algorithms for delivering the curable bone cement at desired flow parameters (e.g., flow rate, temperature, pressure) into a treatment site (e.g., into naturally-occurring cavities in uncompressed cancellous bone of a bone, such as a vertebral body).

As mentioned, some embodiments of bone cement delivery assembly 200 can include an emitter 220. The emitter 220 may apply thermal energy to a flow of bone cement delivered to the cement activation component 215 from chamber 120 of source 122. The thermal energy can cause the viscosity of the cement to increase to a selected, higher viscosity value as the cement exits the needle 124 into bone. The controlled application of energy to bone cement may enable the physician to select a setting rate for the cement to reach a selected polymerization endpoint as the cement is being introduced into the vertebra, thus allowing a high viscosity that will be prevent unwanted cement extravasation.

The cement delivery system can include the cement heating system as disclosed in U.S. patent application Ser. No. 12/062,337, filed Apr. 3, 2008, and the other following related applications: U.S. patent application Ser. No. 11/469,764 filed Sep. 1, 2006; Ser. No. 11/165,652 filed Jun. 24, 2005; App. No. 60/713,521 filed Sep. 1, 2005; Ser. No. 11/209,035 filed Aug. 22, 2005; App. No. 60/929,936 filed Apr. 30, 2007; App. No. 60/899,487 filed Feb. 5, 2007; Ser. No. 12/024,969 filed Feb. 1, 2008; App. No. 60/907,467 filed Apr. 3, 2007; App. No. 60/907,468 filed Apr. 3, 2007; App. No. 60/907,469 filed Apr. 3, 2007; and App. No. 60/929,416 filed Jun. 26, 2007. The entire contents of all of the above applications are hereby incorporated by reference and should be considered a part of this specification.

Figure 3:
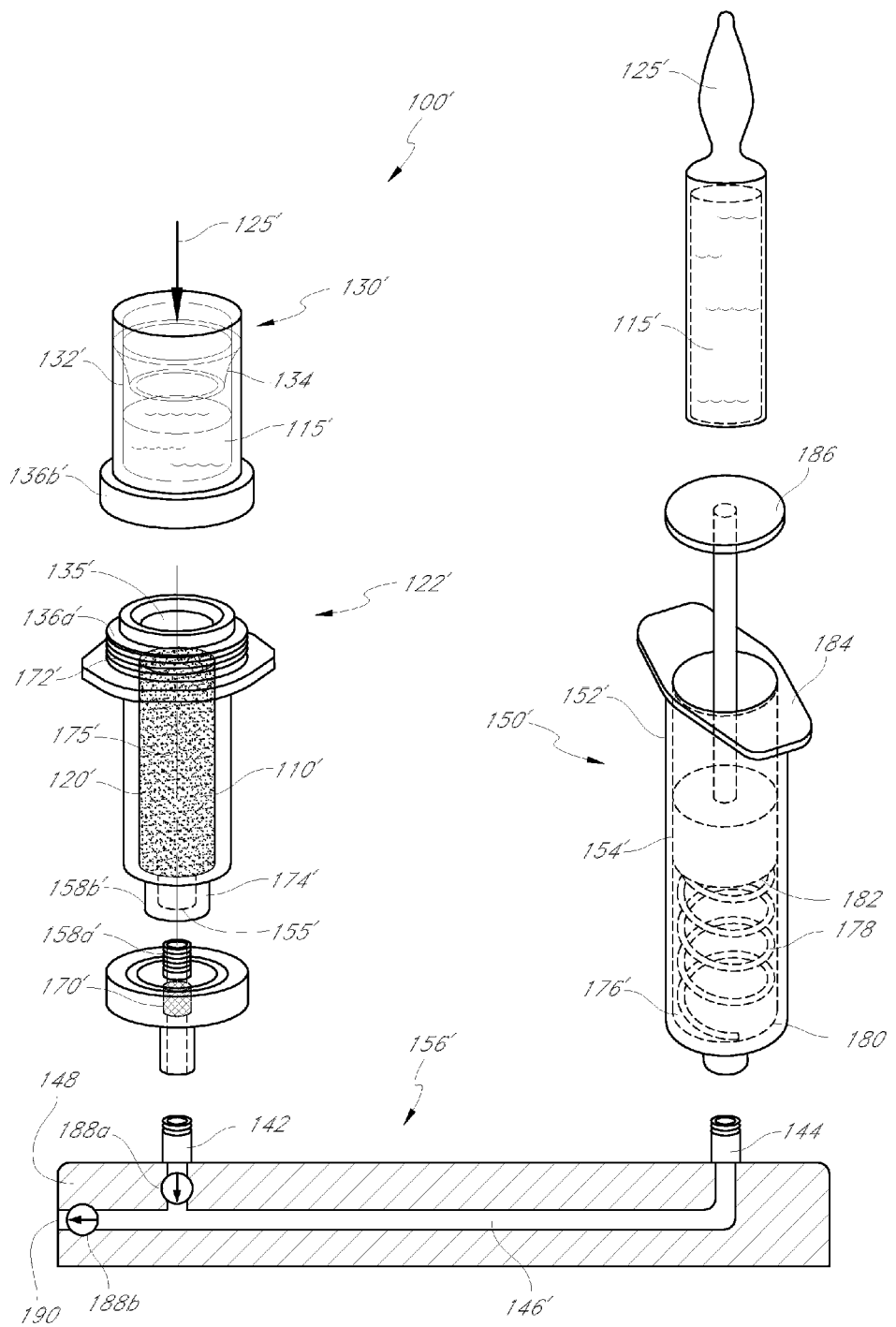
FIG. 3 shows another embodiment of a bone cement preparation system.

Turning now to FIG. 3, another embodiment of a bone cement preparation system 100' will be discussed. In the bone cement preparation system 100', the fitting 156' is in the form of a base 148 to more easily contain and position the system for use. Numerical reference to components is the same as previously described, except that a prime symbol (') has been added to the reference. Where such references occur, it is to be understood that the components are the same or substantially similar to previously-described components. It should be understood that the illustrated bone cement preparation system includes each of the features designated by the numbers used herein. However, as emphasized repeatedly herein, these features need not be present in all embodiments.

The bone cement preparation system 100' includes a cement-carrying body 122' and a receiving body 130'. The proximal end 172' of the cement-carrying body 122' is shown with a threaded fitting 136a' for connecting to the receiving body 130' and for separately connecting to various other devices such as a pressurization mechanism (FIG. 2).

As has been described, a polymer non-liquid component 110' can be positioned within the chamber 120' in the cement-carrying body 122'. A liquid monomer component 115' within an ampule 125' can poured into an inner space 132' of the receiving body 130' to be mixed with the polymer non-liquid component 110'. FIG. 3 also illustrates a funnel 134 that can be used to direct the liquid monomer component 115' to the chamber 120' and thereby to the polymer non-liquid component 110'. In one embodiment, the funnel 134 is removably attachable to the receiving body 130'. The receiving body or the cement-carrying body can define the funnel, which may be either a separate or an integral piece of the receiving body or the cement-carrying body. A first interface surface, such as a seal, though not shown, may also be included at the proximal end 172' of cement-carrying body 122' between the cement-carrying body 122' and the receiving body 130'.

A second interface surface, here a filter 170' is also shown. The filter can be attached to the cement-carrying body 122' at the distal end 174'. The filter 170' can advantageously facilitate the operation of the bone cement preparation system 100' according to some embodiments. The filter 170' can allow air flow therethrough but substantially prevent the flow of liquid monomer therethrough when the monomer 115' has saturated the polymer 110'. In some embodiments, the filter can clog to prevent flow of the liquid monomer. In some embodiments, the cement mixture can clog the filter to prevent flow of the liquid monomer. In other embodiments, the filter may swell or polymerize once contacted by the liquid monomer to prevent flow through the filter. Preferably, the filter will clog, swell, or polymerize only after the bone cement components have been thoroughly and properly mixed.

The bone cement preparation system 100' also includes a fitting 156' that is in the form of a base 148. The base 148 provides a type of docking station that both contains and positions the various components of the system for ease of use (e.g., positions and supports the cement carrying body 122' and vacuum source 150' in a generally vertical position). The base 148 is shown in schematic in FIG. 3 and in perspective in FIG. 4.

The cement-carrying body 122' can connect to the base 148. They may be directly connected, such as being connected with cooperating connectors, such as screw or press-fit coupling portions 142 and 158b, or indirectly connected with the filter 170' positioned between them as shown. The filter 170' is preferably removal from the base 148, such that the base can be reused. Alternatively, the filter 170' can be made integral with the base 148. As has been mentioned, a procedure may require the use of multiple preparations of bone cement. In such a situation, the filter 170' may be replaced (though this may not be required) prior to the preparation of a second, third, etc. container of bone cement with the base being reused throughout the procedure. In other methods, each new bone cement preparation can utilize a new bone cement preparation system 100' including a new base 148. As has been mentioned, in some embodiments, the filter 170' may be designed to clog to prevent flow of the mixed bone cement, thus requiring a new filter 170' to prepare a new container of bone cement.

As shown, the base 148 can position the cement-carrying body 122' and the receiving body 130' in an upright position. In this way gravity can also assist in the transfusion of the liquid monomer component 115' into and through the polymer non-liquid component 110'. This configuration also helps prevent the liquid monomer component 115' from spilling, the bone cement preparation system 100' from tipping over, and/or the bone cement preparation system 100' from having to be held during the entire preparation procedure.

The base 148 can beneficially help the user to operate the system 100' to mix the bone cement components. The base 148 can allow the user to maintain the bone cement components and the vacuum source 150' in an upright position. In this position, the user can then manually actuate the pump-like syringe vacuum source 150' without having to also hold the material container 122'. The base 148 allows the system 100' to be self-supporting (i.e., remains upright and does not need to be held by a user). The system 100' can be configured for manual operation to manually create a vacuum, without requiring the user to hold the system or the saturation chamber in either hand.

The base 148 as shown also includes a flow channel 146' and two one way valves 188a, 188b. The flow channel 146' is connected to the connectors 142 and 144 and has an exit or outlet 190 at or near one way valve 188b. The one way valves 188a, 188b are shown in FIG. 3 with an arrow to indicate the direction of flow. The one way valve 188a allows air to flow into the flow channel 146' through the connector 142, but does not allow air to flow out through this same fitting. The one way valve 188b allows air to flow out of the flow channel 146' at the exit, but does not allow air to flow into the flow channel 146'. Air flow through connector 144 is unrestricted, meaning air can flow both in and out of the connector 144 with respect to the flow channel 146'.

In some embodiments the base is sealed so that the inside space of the base services as the flow channel 146. Alternatively, the flow channel can include one or more of a flexible tube or line, and a solid pathway formed integrally into the base. Other configurations can also be used.

The bone cement preparation system 100' may also have a vacuum source 150'. The vacuum source 150' can take many forms as has been discussed previously. The vacuum source 150' is shown comprising a syringe with a syringe body 152' and a retractable plunger 154'. The retractable plunger 154' is located within a bore 176' of the syringe body 152'. The syringe may comprise a 20 to 60 cc syringe and more particularly a 30 cc syringe. It has been found that a 30 cc syringe can provide a negative pressure of −500 mmHg or greater. The size of the syringe and the amount of desired negative pressure of certain embodiments can vary greatly and can depend on many factors. These factors can include the amount of bone cement to be prepared, the cross-section and length of the mixing chamber and the volume and dimensions of the polymer beads.

The vacuum source 150' can be fixedly or removably attached to the base 148, similar to the filter 170'. In the illustrated embodiment, the vacuum source 150' is a syringe that is attached to the base 148 at a mechanical (e.g., screw or press-fit) coupling portion 144. The syringe body can be fixedly attached to the base 148 to prevent inadvertent unattachment and the associated possible user error while in use. The base 148 may further include a shroud 192 to surround a portion of the attached syringe body as shown in FIG. 4.

Figure 4:
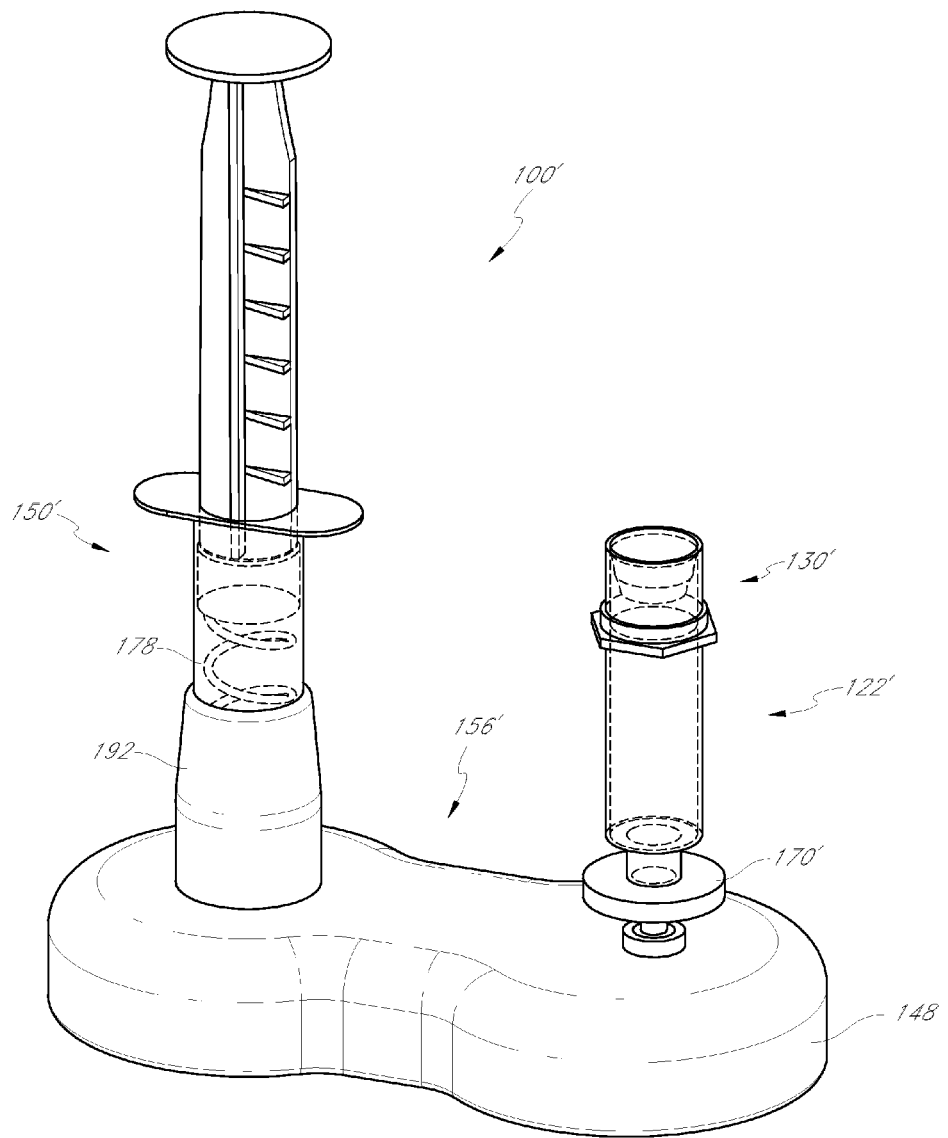
FIG. 4 illustrates a perspective view of another bone cement preparation system.

In FIGS. 3 and 4, a spring 178 is shown in use with the bone cement preparation system 100'. The spring 178 can be connected to the plunger 154'. In this way, the spring 178 can bias and return the plunger 154' to a desired position after it has been moved from the initial position. As shown, the spring 178 can be positioned within the bore 176' of the syringe body 152', such as between a distal end wall 180 of the bore 176' and the distal end 182 of the retractable plunger 154'. In other embodiments, the spring 178 can be positioned outside of the bore 176', such as between the finger grip 184 on the proximal end of the syringe body 152' and the actuation member or thumb pusher 186 at the proximal end of the plunger 154'. The spring 178 can be attached to the syringe in other ways, such as off to the side of the syringe body 152', between some moving portion of the syringe and the base 148, etc. The combined syringe and spring can also be called or considered an air piston.

The spring 178 can take many forms, and may include one or more springs. Some examples include: a coil spring, a leaf spring, an air spring, and a compressible elastic material. The spring can be made out of one or more materials including, metal, rubber, foam, plastic, etc.

An example spring is a metal coil spring having an outer diameter of 0.85 in, a free length of 2.5 in, a solid length of 0.41 in, a spring rate of 4.1 lbs/in, and a maximum compressed force of 8.6 lbs. Another example is a metal coil spring having an outer diameter of 0.875 in, a free length of 3.38 in, a solid length of 0.76 in, a spring rate of 4.7 lbs/in, and a maximum compressed force of 12.3 lbs. Still another example is a metal coil spring having an outer diameter of 0.85 in, a free length of 2.5 in, a solid length of 0.59 in, a spring rate of 8.9 lbs/in, and a maximum compressed force of 16.9 lbs. A final example is a metal coil spring having an outer diameter of 0.859 in, a free length of 3.56 in, a solid length of 0.43 in, a spring rate of 8.4 lbs/in, and a maximum compressed force of 26.3 lbs.

The functioning of a bone cement preparation system 100' according to certain embodiments will now be described. The system 100' can be prepared with the filter 170', cement-carrying body 122', and the receiving body 130' all connected to the base 148 with polymer non-liquid component 110' located in the chamber 120'. A user, such as a nurse or doctor, can then open a monomer source 125' (such as breaking a monomer ampule), and can pour the predetermined volume of monomer 115' into the inner space 132' of the receiving body 130' through the funnel 134.

The user can then actuate the air piston by pushing the plunger 154' downward against the force of the spring 178. In other embodiments, the plunger 154' can be actuated using a hydraulic, pneumatic or motor driven system, the operation of which in some embodiments can be computer controlled. This expels air from the syringe body bore 176' into the flow channel 146'. This in turn causes air to exit the flow channel 146' through the one way valve 188b and outlet 190. The spring then pushes against the plunger 154' moving it towards its initial position creating a vacuum within the syringe body bore 176'. As the one way valve 188b prevents air from entering directly into the flow channel 146', air is drawn in through the one way valve 188a. For example, air can be removed from the polymer non-liquid component 110' within the chamber 120'. This can cause the liquid monomer 115' to be drawn into the polymer non-liquid component 110' into the evacuated space, thereby mixing the two components. The filter 170' catches or prevents flow of the liquid monomer 115', the polymer non-liquid component 110', and the combined bone cement and allows only air to travel through. This step can then be repeated as necessary.

Air may also, especially initially, flow from outside the device through the combined receiving body 130', cement-carrying body 122', and filter 170' to the syringe bore 176'. The filter 170' can become more saturated with each cycle of the air piston. Eventually, the spring force (compressed state) and vacuum pressure are at equilibrium, preventing the piston from returning to its extended position. The equilibrium state can indicate to a user that the filter 170' is fully saturated and that the liquid monomer 115' and polymer non-liquid component 110' are adequately mixed. The spring 178 and spring rate can be adjusted to achieve a desired vacuum pressure equilibrium state that provides an adequate mixture between the liquid monomer 115' and polymer non-liquid component 110'. In some embodiments, the cycling of the air piston can gradually decrease in stroke as the system approaches the equilibrium state.

In some embodiments, the entire mixing process can be done in an interval ranging between about 5 seconds and 60 seconds. The mixing process may require one, two, three or more cycles of the air piston. In particular, the mixing process may require one or two cycles within a complete time period of between about 7 and 11 seconds.

Figure 5:
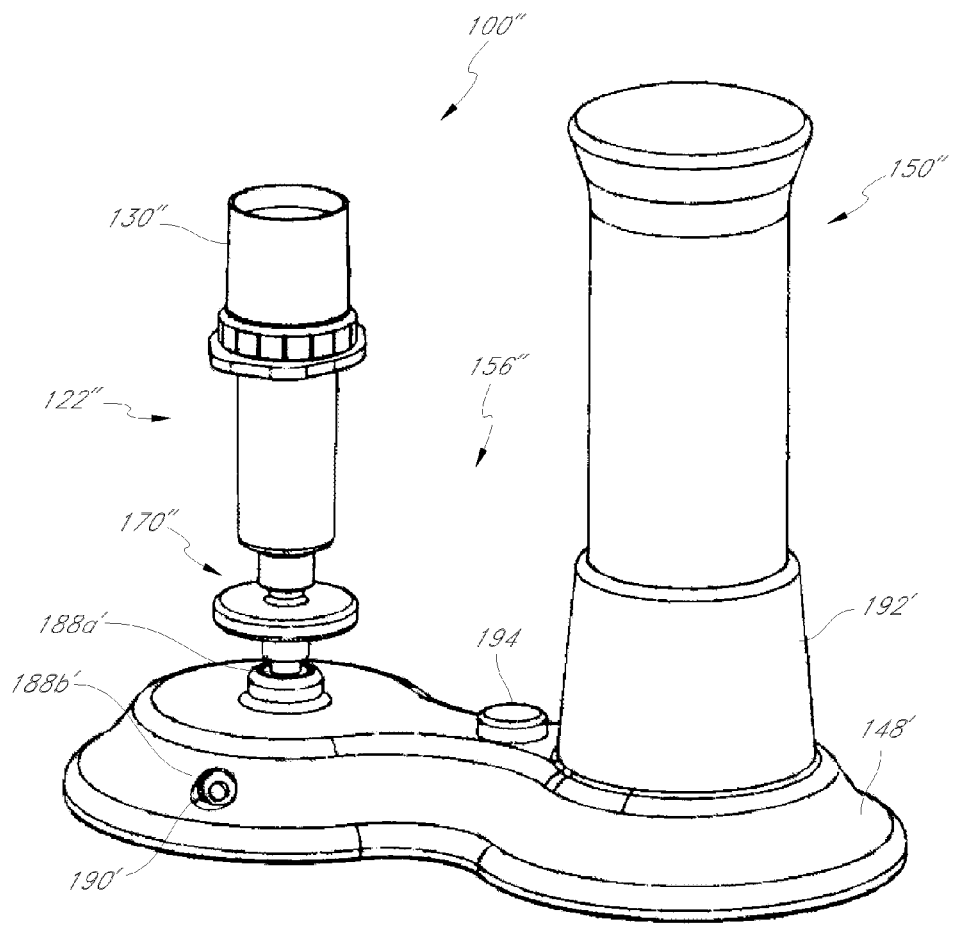
FIG. 5 is a perspective view of still another bone cement preparation system.
Figure 6A:
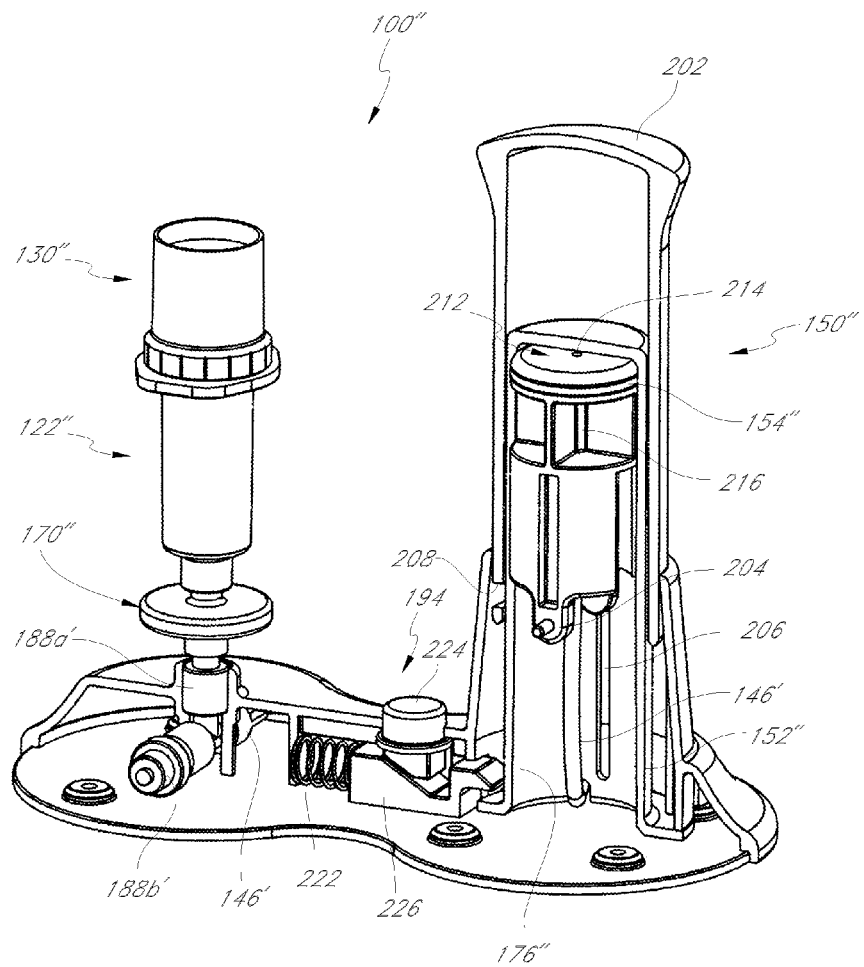
FIGS. 6A-6B illustrate steps in a method of using the bone cement preparation system of FIG. 5, with the bone cement preparation system shown in cross-section.
Figure 6B:
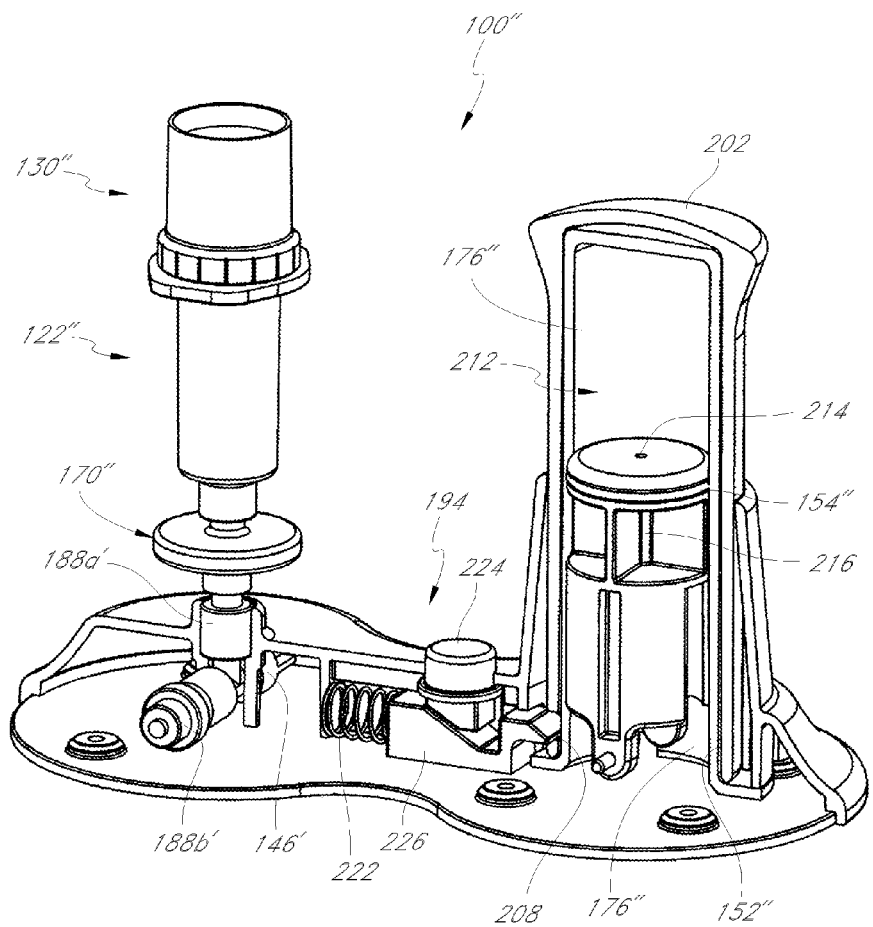

Looking now to FIGS. 5, 6A, and 6B still another bone cement preparation system 100" is shown. Numerical reference to components is the same as previously described, except that an additional prime symbol (') has been added to the reference. Where such references occur, it is to be understood that the components are the same or substantially similar to previously-described components. It should be understood that the illustrated bone cement preparation system includes each of the features designated by the numbers used herein. However, as emphasized repeatedly herein, these features need not be present in all embodiments.

As can be seen, the bone cement preparation system 100" is similar to the system 100' described with reference to FIGS. 3-4. The bone cement preparation system 100" includes a cement-carrying body 122" and a receiving body 130". As has been described, a polymer non-liquid component can be positioned within the cement-carrying body 122" and a liquid monomer component can poured into the receiving body 130" to be mixed with the polymer non-liquid component. The receiving body or the cement-carrying body can define a funnel, which may be either a separate or an integral piece of the receiving body or the cement-carrying body. A filter 170" is also shown attached to the distal end of the cement-carrying body 122". The filter 170" can allow air flow therethrough but substantially prevent the flow of liquid monomer therethrough when the monomer has saturated the polymer as has been described.

A base 148' provides a type of docking station that both contains and positions the various components of the system for ease of use (e.g., positions and supports the cement carrying body 122" and vacuum source 150" in a generally vertical position).

The base 148' can include an internal flow channel 146' and two one way valves 188a', 188b'. As shown, the flow channel 146' is made up of flexible tubing that extends from the vacuum source 150" to the two one way valves 188a', 188b'. The one way valve 188a' allows air to flow into the flow channel 146', but does not allow air to flow out. The one way valve 188b' allows air to flow out of the flow channel 146', but does not allow air to flow into the flow channel 146'.

The vacuum source 150" of the bone cement preparation system 100" will now be discussed. The illustrated vacuum source 150" is similar to vacuum source 150' in that it also provides a manually operated vacuum source to draw the liquid component into the powder component to prepare bone cement, or other two part preparations.

Now comparing FIG. 6A with 6B, it can be seen that pressing down on a actuation member or handle 202 of the vacuum source 150" forces a plunger or piston 154" to also move downward. This increases the size of a vacuum chamber 212 within a bore 176" internal to the vacuum source 150". Increasing the size of the vacuum chamber 212 creates a vacuum within the vacuum chamber 212.

In FIG. 6A the vacuum chamber 212 is almost non-existent because the plunger 154" is positioned within the bore 176" at or near the top of the bore 176". In FIG. 6B it can be seen that the vacuum chamber 212 is now a large empty space within the bore 176". It will be understood that whether or not the vacuum chamber 212 starts with minimal dead space, a large empty chamber, or somewhere in-between, increasing the size of the vacuum chamber 212 from that initial position can create the desired vacuum. One of the benefits of the illustrated vacuum source 150" configuration is that it takes advantage of the initial position of the piston to create a vacuum. Simply pressing on the handle creates a vacuum, without any additional step or delay.

The flow channel 146' can connect to the vacuum chamber 212 in any of a number of different ways. This allows the vacuum chamber 212 and vacuum generated to be in communication with the two one-way valves 188a', 188b', the cement-carrying body 122', and the receiving body 130'. As shown, an opening 214 in the piston 154" is in fluid communication with the vacuum chamber 212 and the flow channel 146'. Thus, a portion of the flow channel 146' extends through or is part of the piston 154". Flexible tubing can connect to the piston 154" and a channel 216 can pass through the piston to the opening 214. In some embodiments the flow channel 146' is connected to a side or top wall of the vacuum chamber 212 rather than passing through the piston. In some embodiments, the flow channel 146' has one or more entry points into the vacuum chamber 212.

The vacuum source 150" can be made up of a cylinder 152" with the handle 202 being in the form of a sleeve that surrounds the cylinder 152". In this configuration, the piston 154" is positioned within the bore 176" of the cylinder 152". The piston 154" can be connected to the handle 202 so that pressing on the handle causes movement at the piston. This connection can be a solid, direct, or indirect connection, among other possibilities. The piston 154" can have a protrusion, extension, rod, or pin 204 that extends from the piston 154" into contact with the handle 202. In FIGS. 6A and 6B, two rods 204 extend from opposite sides of the piston 154". An edge of or hole in the handle sleeve 202 (similar to the slot 208 described below) can engage a rod 204 so that the sleeve 202 and piston 154" move together.

As the piston 154" is located within the cylinder 152", some portion of the connection between the piston 154" and sleeve 202 can pass through the cylinder in someway. For example, the rod(s) 204 can pass through a slot 206 in the cylinder 152". The slot 206 can extend along a portion of the cylinder 152". The slot 206 can be used to guide the piston in its upward and downward movements. As shown, the slot 206 extends in a vertical orientation, though other orientations are also possible such a diagonal, angled, helical, etc. In addition, the slot 206 and rod 204 can be spaced sufficiently far away from the vacuum chamber 212. In this way when the piston is at its farthest extent it generally will not compromise the integrity of the vacuum being created.

The vacuum source 150" can also include a latch or locking mechanism 194. The latch mechanism 194 can hold the handle 202 in the down position. This can allow the vacuum source 150" to continue to draw air into the vacuum chamber 212 until either the latch mechanism 194 is released or the pressure in the vacuum chamber 212 equalizes.

The latch mechanism 194 can take many forms. As illustrated the latch mechanism 194 includes a spring 222, a button 224, and a latch 226. The latch 226 can engage an engagement feature 208 on the sleeve of the handle 202 when the handle is pressed downward. The engagement feature 208 is shown as a slot, but can be a protrusion, ledge, flange, or other feature on or space in the sleeve 202. The button 224 and the latch 226 can have complementary angled or ramped surfaces that are engaged one with the other and allow for relative movement. These complementary angled surfaces can allow the latch mechanism 194 to be released by pressing down on the button 224. This forces the latch 226 backward, releasing the slot 208 and sleeve of the handle 202 from engagement with the latch 226. It will be understood that the latch mechanism 194 can also be used on other embodiments of bone cement preparation systems, such as system 100'.

The bone cement preparation system 100" can function in ways similar to the previously described embodiments. According to certain methods, a user can 1) pour a liquid component into the receiving body 130" to initiate the preparation of bone cement or other two part preparation, where the powder component is already within the cement-carrying body 122"; 2) push the handle 202 downward to create a vacuum; 3) lock the handle 202 in the down position with the latch mechanism 194 to maintain the vacuum; and 4) push the button 224 to release the latch 226 and the vacuum once the liquid component makes contact with the filter 170". The system can beneficially provide a vacuum on the two part preparation for an extended period to facilitate mixing of the components and the drawing of the liquid into the powder. Once the liquid has been sufficiently infused through the powder, any remaining vacuum can be released from acting on the preparation. Once the button 224 has been pressed, any remaining vacuum can act on the piston 154". Thus the vacuum can force the piston 154" to move up, decreasing the size of the vacuum chamber until the pressure in the vacuum chamber equalizes with the environment.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A bone cement preparation system comprising:
    a saturation chamber configured to hold a non-liquid component of a two-part bone cement, the saturation chamber having distal and proximal ends;
    a funnel configured to direct a liquid component of the two-part bone cement to the saturation chamber, the funnel being attached to or part of the proximal end of the saturation chamber;
    a filter positioned at the distal end of the saturation chamber;
    a vacuum source for manually creating a vacuum comprising:
        a housing having an internal cavity;
        a piston positioned within the internal cavity, the piston and the internal cavity forming a vacuum chamber defining a changeable volume whose size is determined by the position of the piston within the internal cavity; and
        an actuation member connected to the piston and movable therewith, the actuation member configured to manually increase the size of the vacuum chamber;
    a base configured to removably or fixedly position the saturation chamber and the vacuum source in an upright position in which the funnel is disposed at a higher vertical position relative to the filter and the size of the vacuum chamber increases when the actuation member moves toward the higher vertical position; and
    a flow channel extending between the filter and the vacuum chamber, the flow channel being in fluid communication with the vacuum chamber and the saturation chamber,
    wherein the system is configured such that increasing the size of the vacuum chamber draws the liquid component into the non-liquid component to combine the components to thereby provide a settable bone cement, and
    wherein the vacuum source and the saturation chamber are part of or connected to the base such that the system is self-supporting and remains upright while manually operated to create a vacuum, without requiring the user to hold the vacuum source or the saturation chamber in either hand.

2. The system of claim 1, wherein the vacuum source is part of the base, the filter is connected to the base and the flow channel extends between them within the base.

3. The system of claim 1, wherein the saturation chamber is detachable from the filter.

4. The system of claim 3, wherein the saturation chamber comprises a syringe body.

5. The system of claim 1, further comprising a spring positioned within the internal cavity of the vacuum source.

6. The system of claim 1, further comprising a first one way valve positioned in the flow channel between the filter and the vacuum source.

7. The system of claim 6, further comprising a second one way valve positioned in the flow channel between an outlet and at least one of the filter and the vacuum source.

8. The system of claim 1, further comprising the non-liquid component and the liquid component combinable to form the settable bone cement.

9. The system of claim 1, wherein the actuation member comprises a thumb pusher and the housing comprises a syringe body.

10. The system of claim 1, wherein the vacuum source is configured such that pressing on the actuation member decreases the size of the vacuum source while increasing the size of the vacuum chamber.

11. A bone cement preparation system comprising:
    a saturation chamber configured to hold a non-liquid component of a two-part bone cement, the saturation chamber having distal and proximal ends;
    a funnel configured to direct a liquid component of the two-part bone cement to the saturation chamber, the funnel being attached to or part of the proximal end of the saturation chamber;
    a filter positioned at the distal end of the saturation chamber;
    a vacuum source for manually creating a vacuum comprising:
        a housing having an internal cavity;
        a piston positioned within the internal cavity, the piston and the internal cavity forming a vacuum chamber defining a changeable volume whose size is determined by the position of the piston within the internal cavity; and
        an actuation member connected to the piston and movable therewith, the actuation member configured to manually increase the size of the vacuum chamber, wherein the actuation member comprises a sleeve surrounding the housing and internal cavity, the sleeve configured to advance up and down over the housing;
    a base configured to position the saturation chamber in an upright position with the funnel at the top and the filter at the bottom, the vacuum source being part of or connected to the base; and
    a flow channel extending between the filter and the vacuum chamber, the flow channel being in fluid communication with the vacuum chamber and the saturation chamber, the system configured such that increasing the size of the vacuum chamber draws the liquid component into the non-liquid component to combine the components to thereby provide a settable bone cement, the system configured for manual operation to manually create a vacuum, without requiring the user to hold the vacuum source or the saturation chamber in either hand.

12. The system of claim 11, wherein the housing comprises a slot and the piston comprises a pin that extends through the slot and is engaged by the sleeve.

13. The system of claim 11, further comprising a locking mechanism to hold the sleeve in a locked position.

14. A bone cement preparation system comprising:
    a base member;
    a saturation chamber configured to hold a powder component of a two-part bone cement, the saturation chamber elongated in a first direction between distal and proximal ends;

a funnel at the proximal end of the saturation chamber configured to direct a liquid component of the two-part bone cement to the saturation chamber;

a filter removably attached to the distal end of the saturation chamber, the filter also attached to the base and configured to secure the saturation chamber to the base in an upright position;

a vacuum source being part of or connected to the base and comprising:
 a housing having an internal cavity;
 a piston positioned within the internal cavity; and
 an actuation member connected to the piston for manually creating a vacuum, wherein the base is configured to removably or fixedly position the vacuum source to extend generally in the first direction such that a vacuum chamber created by the piston in the internal cavity increases in volume when the actuation member moves vertically away from the base in the first direction; and a flow channel extending between the filter and the vacuum source, wherein the system is self-supporting and remains upright while manually operated to create a vacuum, without requiring the user to simultaneously hold the vacuum source and the saturation chamber.

15. The system of claim 14, wherein the saturation chamber comprises a syringe body.

16. The system of claim 14, further comprising a first one way valve positioned in the flow channel between the filter and the vacuum source.

17. The system of claim 16, further comprising a second one way valve positioned in the flow channel between an outlet and at least one of the filter and the vacuum source.

18. The system of claim 14, wherein the vacuum source comprises a syringe.

19. The system of claim 14, wherein the actuation member comprises a sleeve surrounding the housing.

20. The system of claim 14, wherein the funnel is part of the proximal end of the saturation chamber.

21. The system of claim 14, wherein the vacuum source is part of the base and the flow channel extends between the filter and the vacuum source within the base.

22. A bone cement preparation system comprising:
 a base member;
 a saturation chamber configured to hold a powder component of a two-part bone cement, the saturation chamber having distal and proximal ends;
 a funnel at the proximal end of the saturation chamber configured to direct a liquid component of the two-part bone cement to the saturation chamber;
 a filter removably attached to the distal end of the saturation chamber, the filter also attached to the base and configured to secure the saturation chamber to the base in an upright position;
 a vacuum source being part of or connected to the base and comprising:
  a housing having an internal cavity,
  a spring positioned within the internal cavity of the vacuum source, and
  a piston positioned within the internal cavity,
  an actuation member connected to the piston for manually creating a vacuum; and
 a flow channel extending between the filter and the vacuum source, the system configured for manual operation to manually create a vacuum, without requiring the user to simultaneously hold the vacuum source and the saturation chamber.

23. A bone cement preparation system comprising:
 a base member;
 a saturation chamber elongated in a first direction and configured to hold a powder component of a two-part bone cement;
 a funnel configured to direct a liquid component of the two-part bone cement to the saturation chamber;
 a filter removably attached to the saturation chamber, the filter also attached to the base and configured to secure the saturation chamber to the base in an upright position; and
 a vacuum source being part of or connected to the base and being in fluid communication with the saturation chamber, the vacuum source comprising:
  a housing having an internal cavity;
  a piston positioned within the internal cavity; and
  an actuation member connected to the piston for manually creating a vacuum, wherein the base is configured to removably or fixedly position the vacuum source to extend generally in the first direction such that a vacuum chamber created by the piston in the internal cavity increases in volume when the actuation member moves vertically away from the base in the first direction;
 wherein the system is self-supporting and remains upright while manually operated to create a vacuum, without requiring the user to hold the vacuum source or the saturation chamber in either hand.

\* \* \* \* \*